(12) United States Patent
Malinin

(10) Patent No.: US 8,888,823 B1
(45) Date of Patent: Nov. 18, 2014

(54) THIN BENDABLE BONE PLATE FOR BONE DEFICIT REPAIR AND METHOD OF PREPARATION

(71) Applicant: Theodore Malinin, Miami, FL (US)

(72) Inventor: Theodore Malinin, Miami, FL (US)

(\*) Notice: Subject to any disclaimer, the term of this patent is extended or adjusted under 35 U.S.C. 154(b) by 0 days.

(21) Appl. No.: 14/173,495

(22) Filed: Feb. 5, 2014

(51) Int. Cl.
*A61B 17/80* (2006.01)

(52) U.S. Cl.
CPC .................... *A61B 17/8085* (2013.01)
USPC ............................ 606/283; 606/76

(58) Field of Classification Search
USPC .............. 606/76, 283, 909; 623/919
See application file for complete search history.

(56) References Cited

U.S. PATENT DOCUMENTS

| | | | |
|---|---|---|---|
| 4,932,973 A | 6/1990 | Gendler | |
| 5,306,304 A | 4/1994 | Gendler | |
| 5,464,439 A | 11/1995 | Gendler | |
| 5,556,430 A | 9/1996 | Gendler | |
| 6,843,807 B1* | 1/2005 | Boyce et al. | 623/23.51 |
| 8,268,008 B2* | 9/2012 | Betz et al. | 623/23.51 |
| 2009/0269388 A1* | 10/2009 | Sunwoo et al. | 424/423 |
| 2012/0195971 A1* | 8/2012 | Missos et al. | 424/549 |

OTHER PUBLICATIONS

Malinin TI. Acquisition and banking of bone allografts. In Bone Grafts & Bone Substitutes, pp. 206-225. Edited by M.B. Habal and A.H. Reddi. Philadelphia, WB Saunders Company, Aug. 17, 1992.
Malinin, T. & Temple, H. T. Musculoskeletal Tissue Transplantation and Tissue Banking. New Delhi, India: Jaypee Brothers Medical Publishers (P) Ltd., Aug. 28, 2013.

\* cited by examiner

*Primary Examiner* — Andrew Yang
(74) *Attorney, Agent, or Firm* — Akerman LLP

(57) ABSTRACT

A flexible, bendable organic decalcified or partially decalcified bone, cortical or cancellous, adapted for use in augmentation or repair of animal skeletal structures comprising a continuous plate or sheet of natural bone, as well as dermis is described. The thickness, flexibility and tensile strength of the construct is such as to allow it to be shaped and contoured without damage to it. The composition is ultimately remodeled by the body, thus obviating the need for additional surgical intervention. The clinical indications for the use of the invented construct are many, but are particularly prominent in dentistry, oral and maxillofacial surgery and implantology. It is particularly useful in the maxillary sinus augmentation. A unique new method, different from previously described methods for the preparation of the disclosed constructs, is described.

36 Claims, 12 Drawing Sheets

THIN BENDABLE BONE PLATE FOR BONE DEFICIT REPAIR AND METHOD OF PREPARATION

FIELD OF INVENTION

The present invention relates to the preparation of allogeneic, xenogeneic and autologous implants for use in the repair or replacement of portions of the human skeletal system, particularly those formed by membranous ossification. In particular, it is directed toward the use in surgical procedures such as mandibular augmentation, sinus elevation, guided tissue regeneration, closure of nasal oral fistula, closure of the cranial defects and related procedures. The invention discloses implants which cause induction of bone regeneration, as well as the process for making the same.

BACKGROUND

Mammalian bone is made up of matrix in which are encased immature cells as well as osteocytes. The organic portion of the matrix is composed of collagen, polymucosaccarides, osseous channels and related compounds and structures. The inorganic portion of the bone which contributes to the characteristic harness of the bone is hydroxyapatite, a form of calcium phosphate.

If the inorganic component is partially or completely removed, the remaining organic bone matrix can be transplanted into an animal and will reform new bone. No adverse effects are typically associated with such transplantation. The rate of reformation and degree of successful outcomes is variable, however, as each bone has its own requirements for healing, immobilization, and bone grafting. Thus there is a need for improved implants.

SUMMARY OF THE INVENTION

In one aspect, a flexible organic bone plate comprises a continuous sheet of partially or fully decalcified natural bone. The thickness of the sheet may be 1.5 millimeters or less. The sheet may contain a plurality of irregular perforations with serrated edges. In one embodiment, channels radiate out from the plurality of irregular perforations. The plurality of irregular perforations may vary in size and shape. In one embodiment, the plurality of irregular perforations comprise cross-sectional areas defining stellate, quadrangular, triangular or hexagonal shapes, or a mixture thereof. In one embodiment, the thickness of the sheet is between 0.045 millimeters and 1.5 millimeters. In some embodiments, the bone plate is adapted for use in augmentation or repair of animal skeletal structures. The natural bone may be from a mammal. In one embodiment, the mammal is a human. The irregular perforations with serrated edges may be configured to facilitate ingrowth of cells and vasculature from preexisting sources of cartilage or bone tissue at a faster rate compared to a bone sheet of similar thickness having regular perforations without serrated edges. In some embodiments, the bone plate is free-dried.

In another aspect, a process for the production of an organic bone plate having a predetermined thickness comprises decalcifying, either partially or completely, a bone which has been harvested from a bone donor and cutting the bone after the decalcifying into one or more sheets having a thickness 1.5 mm or less. The process may further include harvesting the bone from the bone donor. The bone donor may be a vertebrate, for example. In one embodiment, the vertebrate is a human. The process may further comprise processing the bone to remove substantially all blood and lipid residue prior to the decalcifying. In one embodiment, the decalcifying comprises contacting the bone with EDTA, citric acid, hydrochloric acid, or combinations thereof. In one such embodiment, the decalcifying comprises contacting the bone with citric acid. In another such embodiment, the decalcifying comprises contacting the bone with EDTA and citric acid. In yet another such embodiment, the decalcifying comprises contacting the bone with EDTA, citric acid, and hydrochloric acid. The process may further comprise creating a plurality of irregular perforations having serrated edges on either the bone after the decalcifying or the one or more sheets of the bone after the cutting. In one embodiment, the plurality of perforations are created by punching, burring, drilling, or lasering the sheet. The plurality of perforations may further include channels radiating therefrom. In one embodiment, the plurality of perforations comprise one or more perforations having a cross-sectional area that defines a stellate, quadrangular, triangular or hexagonal shape. In one embodiment, the cutting comprises utilizing a sharp blade to cut the bone.

In yet another aspect, a method for the in vivo repair or replacement of a section of an animal skeletal system comprises affixing, to the section of the animal skeletal system, a flexible organic bone plate comprising a continuous sheet of partially or fully decalcified natural bone having a thickness of 1.5 millimeters or less, wherein the continuous sheet comprises a plurality of irregular perforations having serrated edges defined therein configured to facilitate ingrowth of cells and vasculature from preexisting sources of cartilage or bone tissue at a faster rate compared to a bone sheet of similar thickness having regular perforations without serrated edges. In one embodiment, the one or more irregular perforations having a cross-sectional area defining a stellate, quadrangular, triangular or hexagonal shape. The plurality of irregular perforations may include channels radiating therefrom.

In still yet another aspect, a flexible organic bone plate comprises a continuous sheet of partially or fully decalcified natural bone. The flexible organic plate is obtained by the process of: (i) decalcifying, either partially or completely, a bone from a bone donor; (ii) cutting the decalcified bone from step (i) into one or more sheets of decalcified bone having a thickness of 1.5 mm or less using a sharp blade; and (iii) creating a plurality of irregular perforations having serrated edges on the one or more decalcified bone sheets of step (ii). The irregular perforations may be created by punching, burring or lasering the one or more decalcified bone sheets. The irregular perforations may further comprise a cross-sectional area that defines a stellate, quadrangular, triangular or hexagonal shape. In one embodiment, the process further comprises harvesting the bone from the bone donor. In a further embodiment, the process further comprises creating channels radiating out from the irregular perforations. In one embodiment, the decalcifying comprises contacting the bone with EDTA, citric acid, hydrochloric acid, or combinations thereof In one such embodiment, the decalcifying comprises contacting the bone with citric acid. In another such embodiment, the decalcifying comprises contacting the bone with EDTA and citric acid. In yet another such embodiment, the decalcifying comprises contacting the bone with EDTA and hydrochloric acid.

BRIEF DESCRIPTION OF THE DRAWINGS

FIG. 9(a) illustrates quadrangular perforations. FIG. 9(b) illustrated irregular perforations with channels (black arrows) extending therefrom. FIG. 9(c) illustrates stellate perforations. FIG. 9(d) illustrates regular round perforations for comparison.

FIGS. 10(a) to 10(c) illustrate the flexibility of the decalcified bone plate. FIG. 10(d) illustrates that the bone plate will return to its original shape when straightened out after bending.

DETAILED DESCRIPTION OF THE INVENTION

Described herein are bone plates (sometimes referred to as membranes) and variants thereof. Also described herein are methods and devices for producing bone plates and variants thereof.

While the bone plates of the present disclosure may be referred to as simply bone plates, it is understood that the bone plates comprise organic bone plates, such that a desirable portion of the organic component of the bone has been retained and a significant portion of the inorganic component of the bone has been removed, e.g., completely or partially removed. For example, according to various embodiments, the inorganic portion of the bone may be decalcified by contacting the bone with citric acid, ethylene diamine tetraacetic acid (EDTA), and weak hydrochloric acid. In various embodiments, the contacting of the bone with citric acid is configured such that the citric acid demineralizes the bone slowly and gently to thereby avoid complications, such as destruction of the bone matrix, encountered with the use of strong hydrochloric acid.

As described herein, the completely or partially decalcified bone matrix is preferably sliced into thin sheets. The thin sheets are flexible while retaining tensile strength such that they may be manipulated to desired conformations. Such sheets or membranes further retain many biologic properties related to osteogenesis. According to the present disclosure, such sheets may be prepared using methods that avoid limitations that may be associated with conventional preparation techniques that, for example, require precutting un-decalcified sheets with an expensive diamond saw blade or conventional microtome intended for making sections for histological examination. Rather, the present disclosure described cutting bone decalcified with citric acid or by other methods with a sharp thin blade. As will become more clear below, the methods of the present disclosure may therefore prepare bone plates in which beneficial proteins associated with the bone may be retained to a greater degree due to the avoidance of contacting the bone with strong acid and creating excessive heat when sectioning the bone, e.g., prior to decalcification or with a saw or conventional microtome knife.

Figure 1:
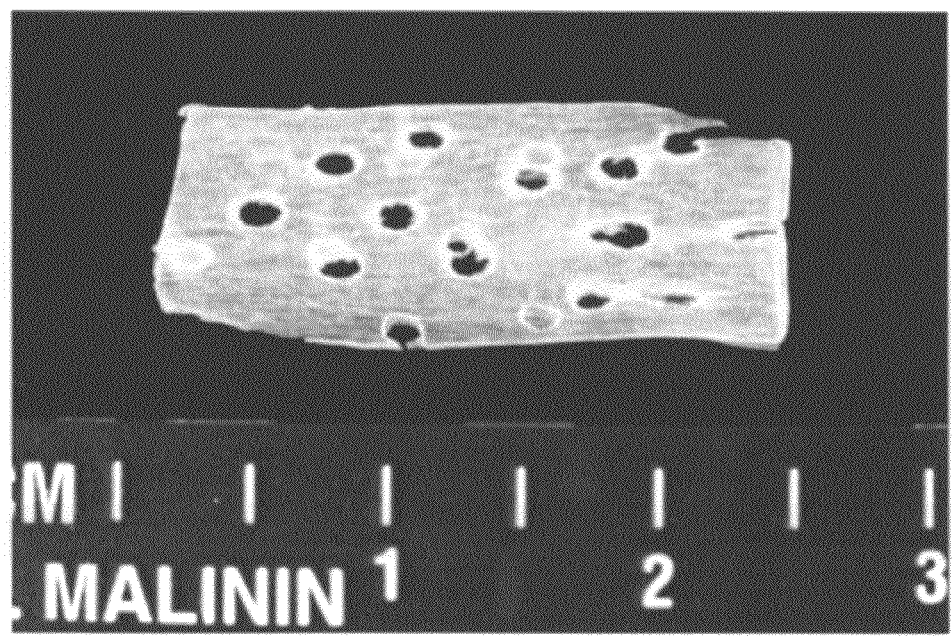
FIG. 1. Decalcified bendable cortical bone plate with round perforations according to various embodiments.

According to various embodiments, a bone plate comprises organic bone formed in a continuous sheet of partially or fully decalcified natural bone. The bone plate may further include one or more artificial perforations defined therein. For example, FIG. 1 depicts decalcified bone comprising flexible or bendable characteristics comprising cortical bone plate having round perforations produced by the device depicted in FIG. 2. Such a device may be used for producing round holes, or as described below, irregular holes in decalcified bone plates or membranes or for making perforations in freeze-dried dermis or other membranous structures according to various embodiments. For example, according to various embodiments, the shape of the perforations may be altered by changing the shape of tubes used to produce the holes or perforations.

Figure 3:
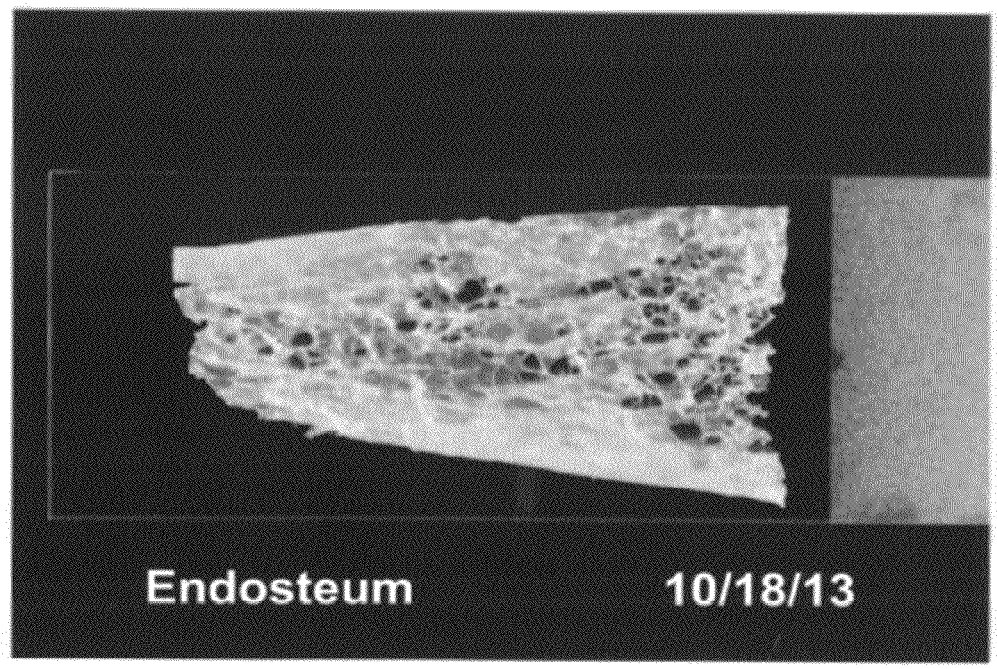
FIG. 3. Decalcified cancellous bone plate. Trebeculae serve as perforations. These plates are prepared from endosteum according to various embodiments.
Figure 4:
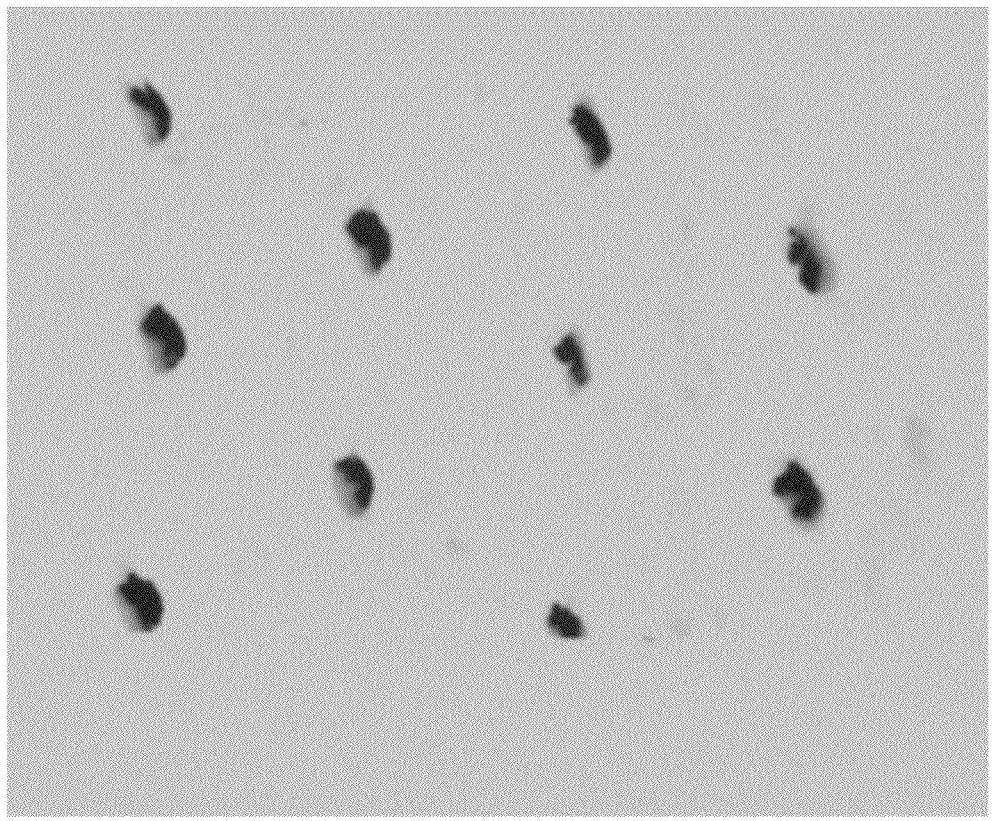
FIG. 4. Irregular perforations in freeze-dried dermis according to various embodiments, FIG. 5. Decalcified cortical bone being cut with a sharp blade in a Steddy-Riggs sectioning device according to various embodiments.
Figure 9A:
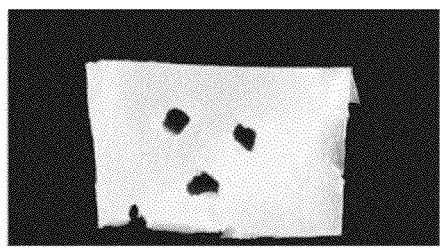
FIGS. 9a-9d: Decalcified bone plates showing irregular perforations according to various embodiments.
Figure 9B:
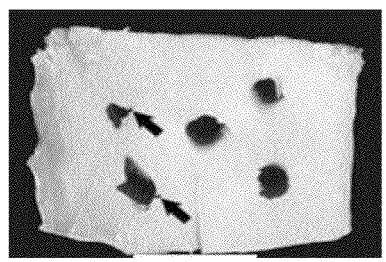
Figure 9C:
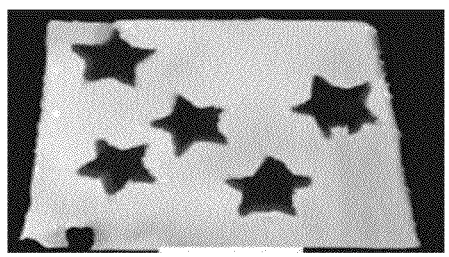
Figure 9D:
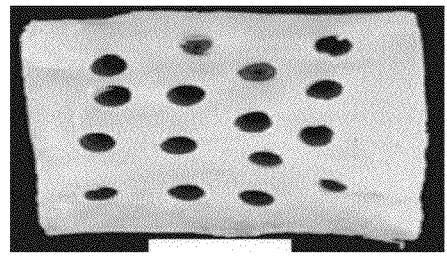

According to various embodiments, the perforations preferably define irregular rather than round cross-sectional areas, which may be further defined by uneven edges. FIG. 3 depicts another embodiment of a decalcified cancellous bone plate prepared from endosteum according to various embodiments. In this embodiment, trebeculae serve as perforations. In certain embodiments, the bone plate comprises one or more artificial perforations having uneven edges that define irregular cross-sectional areas. In further embodiments, the uneven edges comprise serrated edges from which slits (or channels) may further radiate in different directions to thereby form a series of canals radiating from the serrated edges of the irregular perforations, as shown in FIGS. 4 and FIG. 9b.

Figure 2:
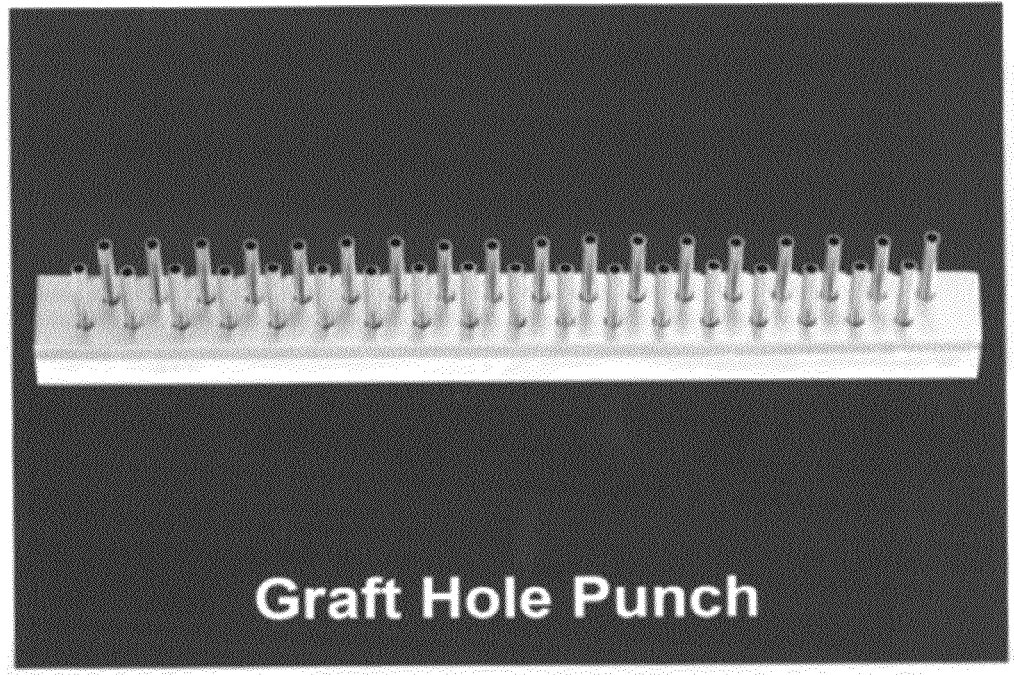
FIG. 2. Device for producing round holes in decalcified bone plates or membranes or for making perforations in freeze-dried dermis or other membranous structures according to various embodiments. The shape of the perforations can be altered by changing the shape of tubes used to produce the holes.

According to various embodiments, a method of preparing the bone plate comprises creating perforations by punching, burring, lasering or otherwise forming the perforations on the bone using, for example, a punch, burring or perforating implement, laser, or similar devices. For example, in some embodiments, a device comprising a plurality of perforating members defining one or more perforation shapes, such as a round perforation shape as illustrated in FIG. 2 or an irregular shape, may be used to form perforations on the bone, preferably in bone that has been decalcified. In certain embodiments, the slits forming the canals radiating from the perforations on the surfaces of the construct may be formed thereon by stationary drills, blades, saws, laser or similar devices.

It is noted that, according to various embodiments, the bone plate according to the present disclosure may be employed as allografts, autografts, or xenografts in transplantation procedures. For example, the bone plates or variants thereof, comprising irregular perforations defined by serrated or uneven edges having canals radiating therefrom, as herein described, may beneficially facilitate ingrowth of the cells and vasculature from the host bed into which the construct is implanted. Such ingrowth may include ingrowth which is accelerated compared to bone plates having conventional round perforations with even edges. According to various embodiments, density or number of perforations may be varied or consistent.

In various embodiments, the bone plate as described above may be further characterized by flexibility. For example, the bone plate may comprise flexibility such that it may bend or flex. In some embodiments, flexibility may comprise malleability, such that the bone plate may be bendable while retaining its tensile strength into a desired form, shape, or suitable conformation. In one embodiment, flexibility comprises a degree of elasticity or reversible deformation as a result of application and removal of stress, e.g., shear, tensile, or compressive stress. For example, the bone plate may be flexibly bent or strained into a bent or folded conformation. Upon removal of the stress, the bone plate may then retain a portion of its pre-stress form. In the above embodiments or another embodiment, the flexibility of the bone plate may comprise the ability to be shaped or formed into sequential first, second, or third conformations upon application of sequential stresses configured to transition the bone plate into such sequential conformations. Thus, in one embodiment, the bone plate comprises a flexible continuous sheet of partially or fully decalcified natural bone. The thickness of the sheet, for example, may be 1.5 millimeters or less. In one embodiment, the sheet comprises a plurality of irregular perforations with serrated edges as described above.

In various embodiments, the bone plate may be freeze-dried and thus comprise a freeze-dried organic bone plate comprising a continuous sheet of partially or fully decalcified natural bone, wherein the thickness of the sheet is 1.5 millimeters or less and wherein the sheet contains a plurality of irregular perforations with serrated edges having canals radiating therefrom. As described above, the bone plate according to the present disclosure is also flexible.

As introduced above, in certain embodiments, the bone plate comprises channels radiating out from the serrated edges of the irregular perforations, such as is set forth in FIG. 9b. Such irregular perforations may vary in shape and size. For example, the irregular perforations may comprise stellate, quadrangular, triangular or hexagonal perforations, or mixtures thereof. This list, however, is non-limiting. Such irregular perforations with serrated edges may be configured to facilitate ingrowth of cells and vasculature from preexisting sources of cartilage or bone tissue at a faster rate when compared to a bone sheet of similar thickness having regular perforations without serrated edges.

As introduced above, the bone plate may comprise a continuous sheet of partially or fully decalcified natural bone. In various embodiments, the thickness of the sheet is between 0.45 millimeters and 1.5 millimeters. In an embodiment, the thickness of the sheet may be between 0.045 to 1.0 millimeters, 1.0 millimeters to 1.5 millimeters, 0.75-1.25 millimeters and so forth. For example, in one embodiment, the thickness of the sheet may be between about 1.25 millimeters to about 3.0 millimeters or thicker. Such ranges are used as shorthand for describing each and every value that is in that range. Any value within the range can be selected as the terminus of the range.

In an embodiment, the natural bone is from a mammal, including a human. In an embodiment, the bone is cancellous bone. In another embodiment, the bone is cortical bone.

In any of the above embodiments, the bone plate is adapted for use in augmentation or repair of animal skeletal structures.

Figure 10A:
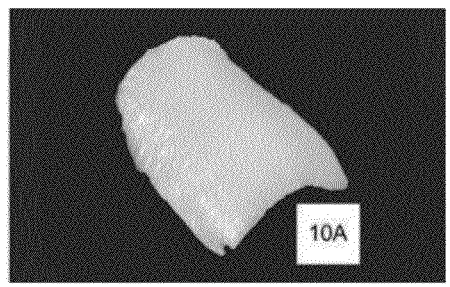
FIGS. 10a-10d illustrate the flexible, bendable, malleable bone plate according to various embodiments.
Figure 10B:
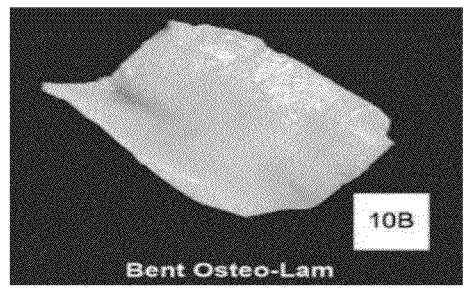
Figure 10C:
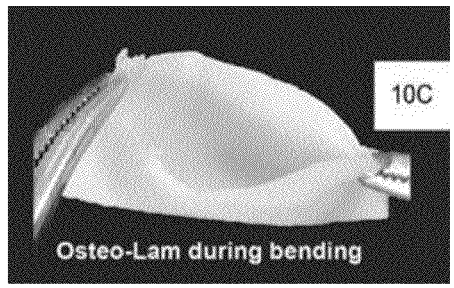
Figure 10D:
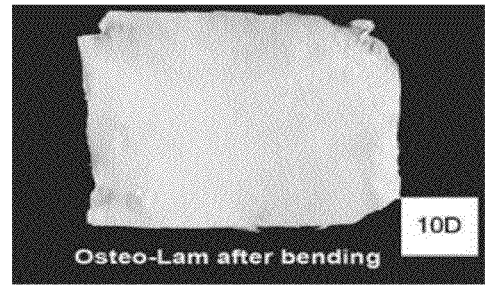
Figure 11:
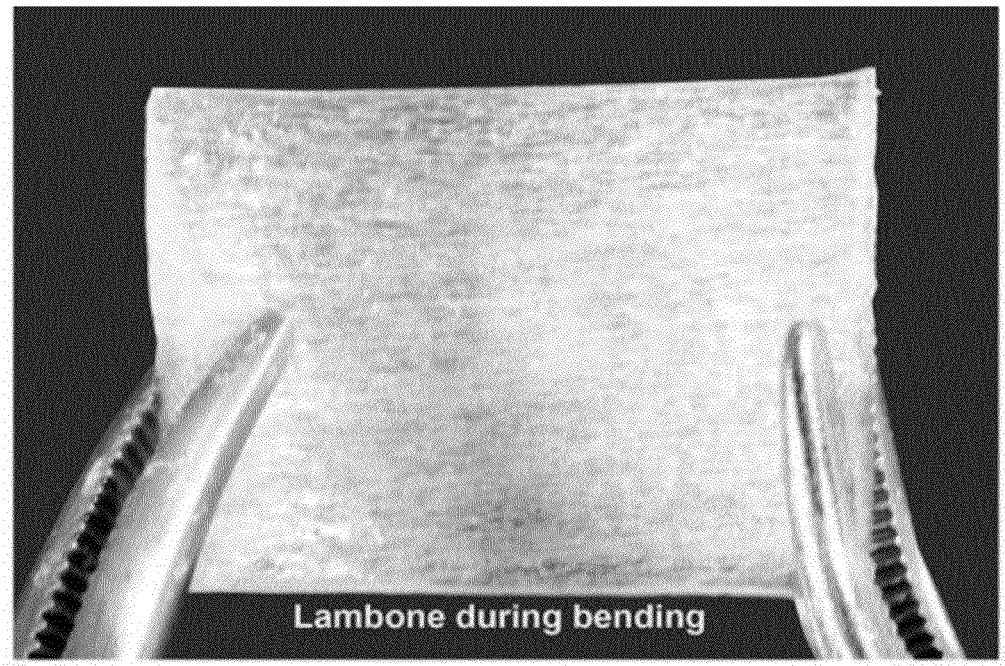
FIG. 11 illustrates the bone plate of the prior art which is rigid and stiff thus allowing it to be bent only to a small degree.
Figure 12:
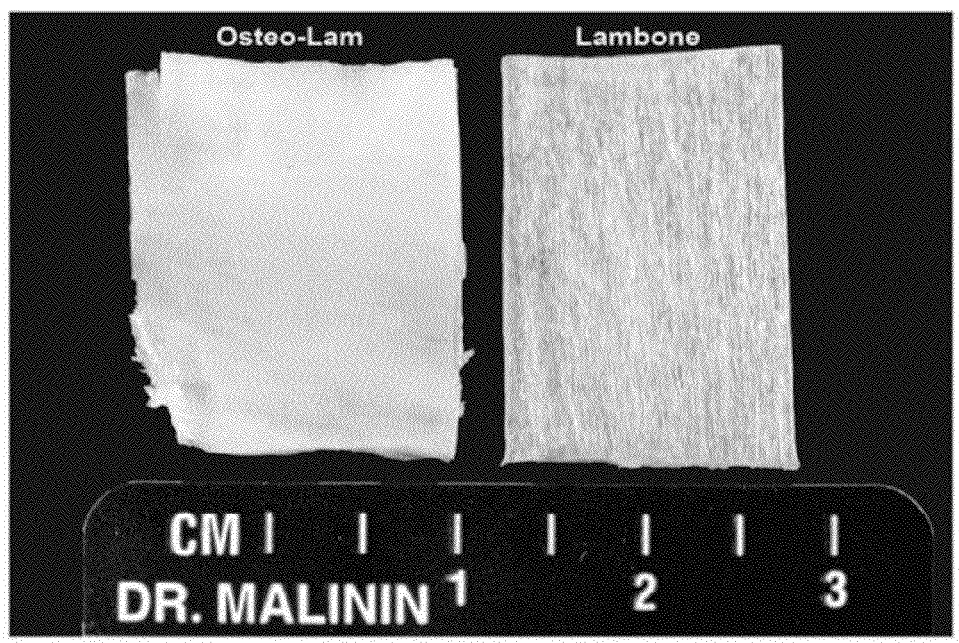
FIG. 12 illustrates a comparison of the bone plate depicted in FIGS. 10a-10d and the prior art bone plate depicted in FIG. 11.

The flexible organic bone plate described herein exhibits superior flexibility over those of the prior art. For example, as shown in FIG. 10C, the bone plate may be bent without fracturing. The bone plate may be formed into bent or folded conformations as shown in FIGS. 10A and 10B. The bone plate may also return to its original shape when straightened out, as showing in FIG. 10D.

Figure 5:
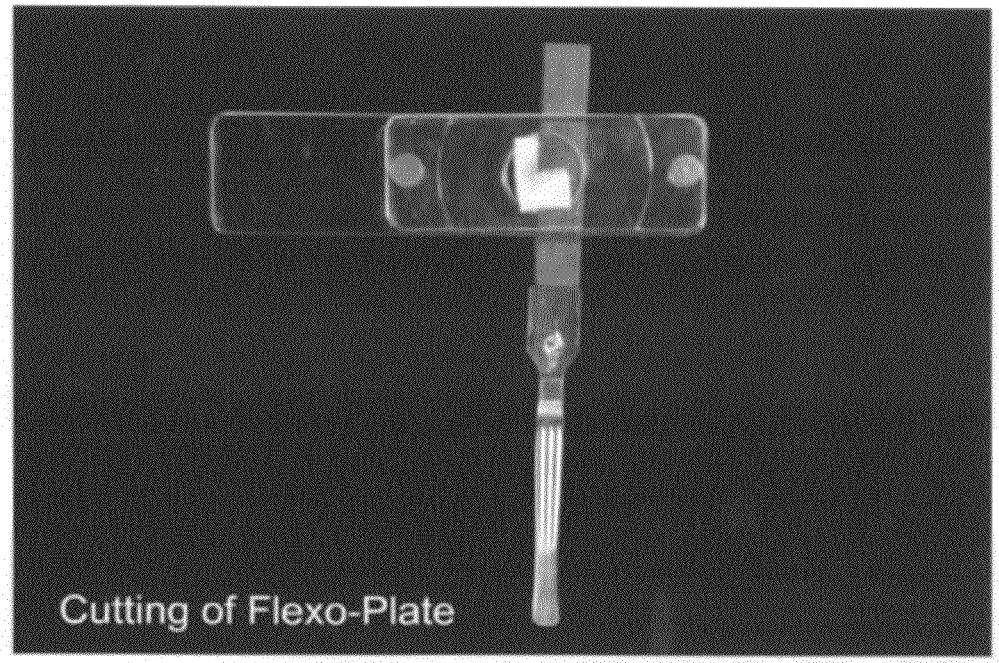
Figure 6:
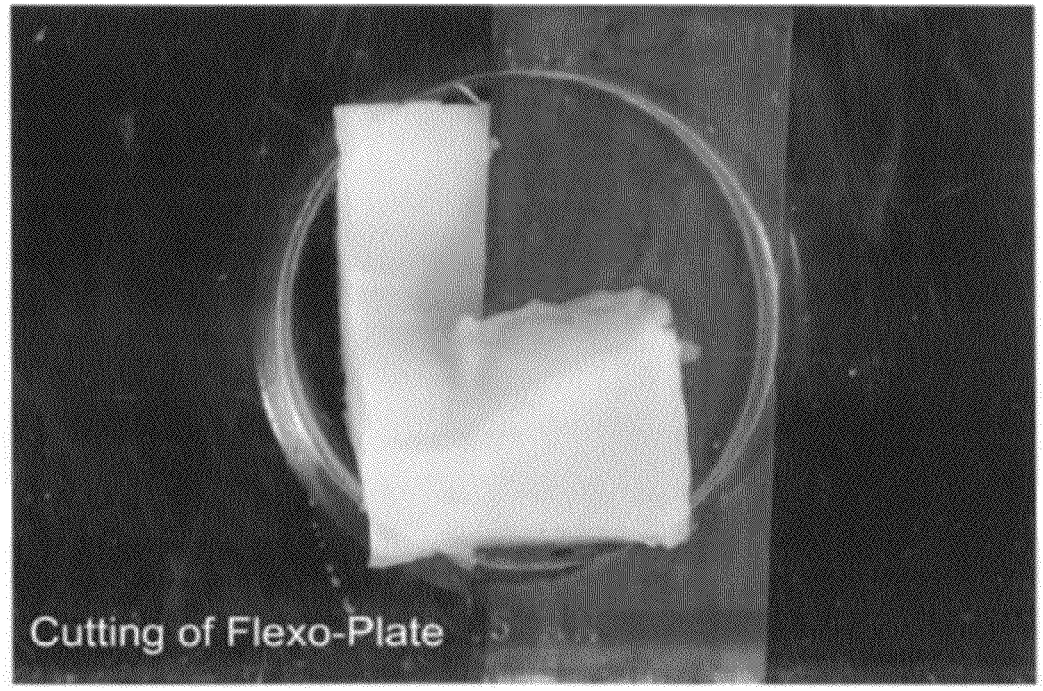
FIG. 6. Close-up view of decalcified cortical bone cut with a sharp blade according to various embodiments.
Figure 7:
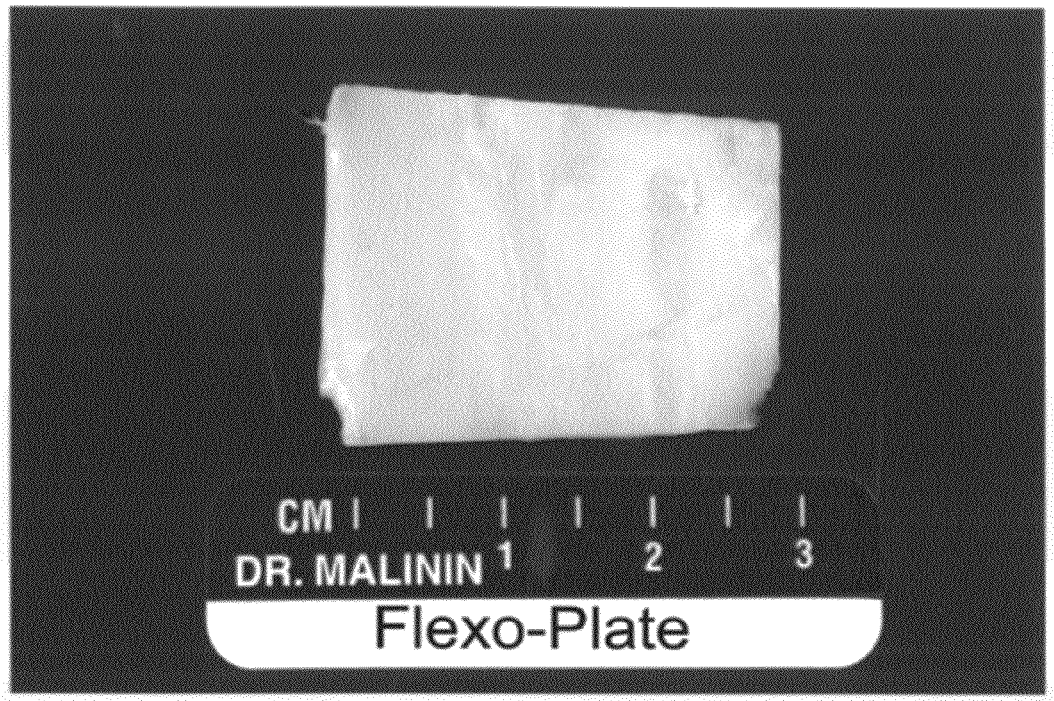
FIG. 7. Decalcified cortical bone plate 0.85 mm in thickness before it is perforated according to various embodiments.
Figure 8:
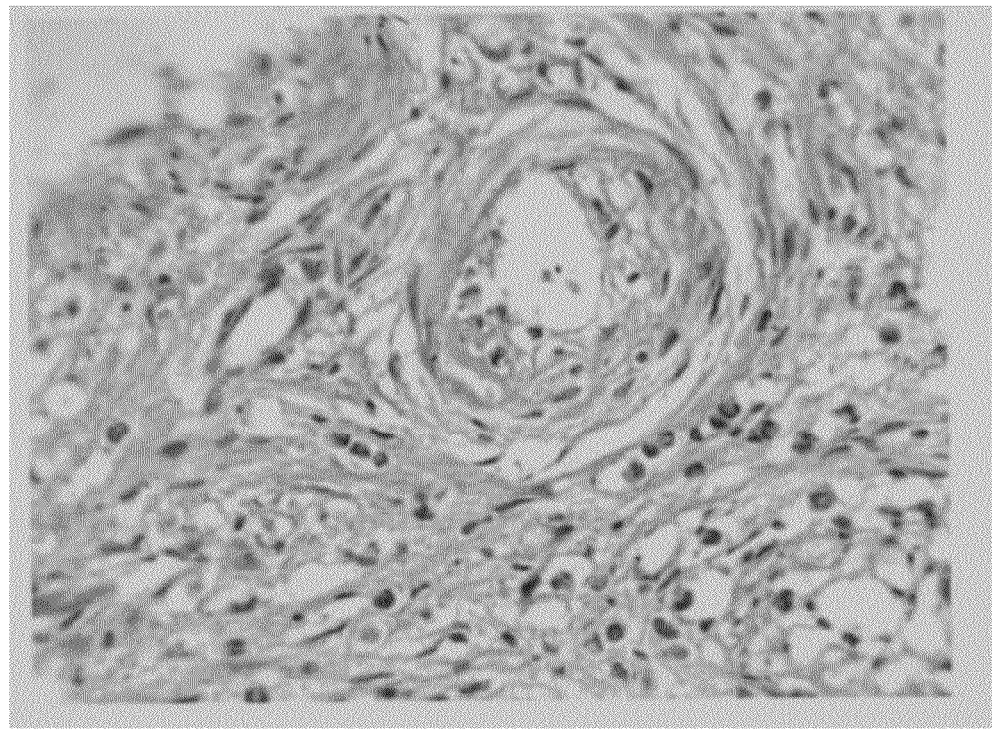
FIG. 8. Microscopic section of a decalcified freeze-dried flexible cortical bone plate four weeks post-implantation into an experimental animal according to various embodiments. The perforation in the center has been replaced with vascularized mesenchymal tissue of the host. Bone matrix contains osteoprogenitor cells of the host.

Also provided are methods for making flexible organic bone plates which comprise a continuous sheet of partially or fully decalcified natural bone. This optionally includes excising an entire bone or part of a bone from a bone donor. In various embodiments, the donor can be either human (allogeneic) and animal (xenogeneic). A harvested or excised bone may be processed immediately or preserved according to any known preservation method including freezing, freeze-drying, hypothermic dehydration, chemical dehydration, immersion in a chemical solutions, etc. Partial or complete decalcification is carried out on thin bone plates, strips or other configurations. Decalcification can be carried out by exposing bone to citric acid, ethylene diamine tetraacetic acid (EDTA) and weak hydrochloric acid, or by other methods A method of producing a flexible organic bone plate comprise decalcifying the bone, as described herein, and subsequently cutting the decalcified bone with a sharp blade. This process is further illustrated in FIGS. 5-7. FIG. 5 shows flexible decalcified bone positioned between two plastic plates bone plates of a Stadie-Riggs tissue slicer. A sharp blade is positioned between the two plastic plates and is slidable to section the bone, as illustrated in FIG. 6, into thin sheets of desired thickness, an example of which is provide in FIG. 7. Such thin sheets of decalcified bone made by this process support growth of human cells in vivo as set forth in FIG. 8 and produce osteogenesis in experimental animals. In addition, the serrated perforations with radial channels improve and facilitate the osteogenesis process. This method avoids the need to cut un-decalcified bone with a diamond saw blade, or a conventional microtome. By first decalcifying the bone, using, for example, citric acid or any other method disclosed herein, the decalcified bone can be cut with a sharp blade rather than a saw or conventional microtome knife. Thus it avoids the use of an expensive precision saw and diamond blade. Sectioning of bone with a bone saw creates heat which deactivates some proteins, despite the use of irrigation during the process. The method of the present invention, by decalcifying first and then cutting with a sharp blade, does not create heat and avoids the deactivation of proteins.

Thus, in one embodiment, the invention can comprise a process for the production of an organic bone plate having a predetermined thickness comprising: (i) decalcifying, either partially or completely, a bone which has been harvested from a bone donor; and (ii) cutting the decalcified bone from step (i) into sheets having a thickness of 1.5 mm or less.

Also provided is a flexible perforated organic bone plate comprising a continuous sheet of partially or fully decalcified natural bone, wherein the flexible perforated organic plate matrix is obtained by the process of described herein. For example, in an embodiment the process comprises: (i) decalcifying, either partially or completely, an entire or part of a bone from a bone donor; (ii) cutting the decalcified bone from step (i) into sheets having a thickness of 1.5 mm or less using a sharp blade; and (iii) creating a plurality of irregular perforations with serrated edges on the decalcified bone sheet of step (ii).

The present invention provides for decalcifying the bone with citric acid, ethylene diamine tetraacetic acid (EDTA) and weak hydrochloric acid. Citric acid decalcifies bone slowly and gently and avoids the complications, such as complete destruction of the bone matrix, encountered with strong hydrochloric acid. Citric acid does not produce deleterious effects on humans. Bone decalcified with citric acid, EDTA, or combinations thereof, with or without and hydrochloric acid can be cut with a sharp blade. For example, the decalcified bone can be placed between two rigid plates, e.g., rigid plastic or metal plates, and cut with a sharp blade. Alternatively, bone can be rigidly held in a vice or other device and cut by guided blades, for example. The thickness of the preparations, for example, as shown in FIG. 1, so obtained varies between 0.45 mm to 1.5 mm.

Thus, in an embodiment, the decalcification of the bone in step (i) comprises decalcifying the bone with EDTA, citric acid, hydrochloric acid, or combinations thereof or by other decalcifying methods. In an embodiment, the bone is decalcified with citric acid. In another embodiment, the bone is decalcified with EDTA and citric acid. In a further embodiment, the bone is decalcified with citric acid, EDTA and weak hydrochloric acid. in various embodiments, decalcifying bone as herein disclosed avoids over-decalcification of the bone thereby improving flexibility of the bone preparation compared to bone preparations prepared by conventional methods.

In a further embodiment, the method comprises cutting the decalcified bone with a sharp blade. As used herein, sharp blade includes, but is not limited to thin flexible blades such as those manufactured by Lipshaw, scalpels, thin knife blades, wires, or laser devices. According to various embodiments, a sharp blade does not include a bone saw or conventional microtome.

In one embodiment, preparing the bone plate further comprises creating a plurality of irregular perforations having serrated edges on or through the bone sheet after either decalcifying the bone or cutting the decalcified bone. In certain embodiments, the irregular perforations are created by punching, burring, drilling, or lasering the sheet. In some embodiments, the plurality of irregular perforations include channels radiating therefrom. In one embodiment, the plurality of irregular perforations comprise perforations having cross-sectional areas defining stellate, quadrangular, triangular, or hexagonal shapes, or combinations thereof. It is to be appreciated, however, that the cross-sectional area of the irregular perforations may define additional geometric shapes as well as non-geometric shapes.

In one embodiment, the process further comprises harvesting a bone from a donor, which may include a defined unit of bone or part of a defined unit of bone excised from the bone donor. In various embodiments, harvesting a bone may comprise excising bone from a donor bone, which may include a defined unit of bone or a part of a defined unit of bone harvested from a bone donor. In certain embodiments, the bone donor is a vertebrate. In one embodiment, for example, the vertebrate is a human. Methods for harvesting a bone, or part of a bone, from a bone donor are known in the art, e.g., as described in Malinin, T. & Temple, H. T. (2013). *Musculoskeletal Tissue Transplantation and Tissue Banking*. New Delhi, India: Jaypee Brothers Medical Pub., the contents of which are here incorporated by reference in its entirety. Common donor sites from which donor bone may be harvested include, but are not limited to, the ilium, tibia, fibula, and ribs. In addition, the bone may be harvested from the mandible of the vertebrate. In an embodiment, the bone is cancellous bone. In another embodiment, the bone is cortical bone.

In some embodiments, the process further comprises processing the harvested bone to remove substantially all blood and lipid residue prior to the decalcification of the harvested bone. Such processing methods are known in the art, e.g., as described in Malinin, T. & Temple, H. T. (2013). *Musculoskeletal Tissue Transplantation and Tissue Banking*. New Delhi, India: Jaypee Brothers Medical Pub.

In a further embodiment, the process comprises freeze drying the resulting organic bone plate. Methods for preparing freeze dried sections of decalcified bone are known in the art, such as those described in Malinin, T. I. (1992). Acquisition and banking of bone allografts. In Habal M B, Reddi A H (Eds.), *Bone grafts and bone substitutes* (pp. 206-233). Philadelphia, Pa.: W.B. Saunders Co., which is hereby incorporated by reference in its entirety.

According to various embodiments, the bone plate of the present disclosure may be employed in surgical procedures such as mandibular augmentation, sinus elevation, guided tissue regeneration, closure of nasal oral fistula, closure of cranial defects, among others. The bone plate prepared and comprising the characteristic features as herein described may comprise a construct suitable for use as an implant configured to beneficially promote induction of bone regeneration superior to certain conventional constructs prepared by more expensive or complex methods.

In various embodiments, a method for the in vivo repair or replacement of a section of an animal skeletal system is disclosed. The method may comprise affixing to the section a flexible perforated organic bone plate comprising a continuous sheet of partially or fully decalcified natural bone, as described herein. In one embodiment, the bone plate contains a plurality of irregular perforations with serrated edges, such as, for example, stellate, quadrangular, triangular or hexagonal perforations. In a further embodiment, the plurality of irregular perforations contains channels radiating therefrom and the surface can be scored in a gull wing or similar pattern.

In view of the above description and examples below, one of ordinary skill in the art will be able to practice the invention as claimed without undue experimentation. The foregoing will be better understood with reference to the following examples that detail certain embodiments of the invention. All references made to these examples are for the purposes of illustration and not limitation. The following examples should not be considered exhaustive or exclusive, but merely illustrative.

EXAMPLES

Example 1

Excision and Preparation of a Donor Bone

The bone was excised under aseptic conditions from cadaver bone. The bone was washed and the periosteum was removed. The bone marrow was removed with metal brushes and the medullary cavity was washed out with copious irrigation. Microbiological studies were conducted to assure sterility and laboratory tests were performed on the donor.

Example 2

Preparation of Freeze-Dried, Decalcified, Flexible Bone Plates from Donor Bone

The bone prepared in Example 1 was wrapped and quick frozen by placement it into vapor phase of liquid nitrogen. After all microbiological studies to assure sterility were completed, and laboratory reports on the donor received, the bone was placed on a pre-cooled shelf ($-40°$ C.) of a freeze-dryer and the vacuum pump turned on. The chamber of the freeze-dryer was maintained at 100 millitorr of vacuum, and the condenser at $-70°$ C. The freeze-drying cycle was 14 days. During the last two days of the cycle the shelf temperature was brought up to $25°$ C. The bone was removed from the freeze-dryer following the freeze-drying cycle and was sectioned into 3 individual plates. These bone plates were placed into 10% v/w solution of citric acid for 48 hours and then transferred to solutions of 5% v/w of EDTA and finally into 10.5 N HCl for 48 hours in each. Following removal of the bone plates from the HCl solution, the bone plates where cut in a Stadie-Riggs tissue slicer, as shown in FIGS. 5 & 6. Perforations in decalcified bone were made with specially prepared punches.

Example 3

Implantation of Freeze-Dried, Decalcified, Flexible Bone Plates into an Experimental Animal Freeze-dried, decalcified, flexible bone plates with round perforations prepared at described in Examples 1 and 2 where implanted intramuscularly into athymic rats. The animals were sacrificed at 2, 4, and 6 weeks post-implantation and implants removed with surrounding soft tissues. The implants and surrounding soft tissue were x-rayed, photographed and fixed in 10% formalin in Earle's balanced salt solution. Paraffin embedded tissues were section on rotary microtomes at 5-6 microns, and stained with hematoxylin and eosin and "special stains" as needed.

What is claimed is:

1. A flexible organic bone plate comprising a continuous sheet of partially or fully decalcified natural bone, wherein the thickness of the sheet is 1.5 millimeters or less, and wherein the sheet contains a plurality of irregular perforations with serrated edges.

2. The flexible organic bone plate of claim 1, further comprising channels radiating out from the plurality of irregular perforations.

3. The flexible organic bone plate of claim 1, wherein the plurality of irregular perforations vary in size and shape.

4. The flexible organic bone plate of claim 1, wherein the plurality of irregular perforations comprise cross-sectional areas defining stellate, quadrangular, triangular or hexagonal shapes, or a mixture thereof.

5. The flexible organic bone of claim 1, wherein the thickness of the sheet is between 0.045 millimeters and 1.5 millimeters.

6. The flexible organic bone plate of claim 1, wherein the bone plate is adapted for use in augmentation or repair of animal skeletal structures.

7. The flexible organic bone plate of claim 1, wherein the natural bone is from a mammal.

8. The flexible organic bone plate of claim 7, wherein the mammal is a human.

9. The flexible organic bone plate of claim 1, wherein the irregular perforations with serrated edges are configured to facilitate ingrowth of cells and vasculature from preexisting sources of cartilage or bone tissue at a faster rate compared to a bone sheet of similar thickness having regular perforations without serrated edges.

10. The flexible organic bone plate of claim 1, wherein the bone plate is free-dried.

11. A process for the production of an organic bone plate having a predetermined thickness comprising:
 (i) decalcifying, either partially or completely, a bone which has been harvested from a bone donor; and
 (ii) cutting the bone after the decalcifying into one or more sheets having a thickness 1.5 mm or less.

12. The process of claim 11, further comprising harvesting the bone from the bone donor.

13. The process of claim 12, wherein the bone donor is a vertebrate.

14. The process of claim 13, wherein the vertebrate is a human.

15. The process of claim 11, further comprising processing the bone to remove substantially all blood and lipid residue prior to the decalcifying.

16. The process of claim 11, wherein the decalcifying comprises contacting the bone with EDTA, citric acid, hydrochloric acid, or combinations thereof.

17. The process of claim 16, wherein the decalcifying comprises contacting the bone with citric acid.

18. The process of claim 16, wherein the decalcifying comprises contacting the bone with EDTA and citric acid.

19. The process of claim 16, wherein the decalcifying comprises contacting the bone with EDTA, citric acid, and hydrochloric acid.

20. The process of claim 11, further comprising creating a plurality of irregular perforations having serrated edges on either the bone after the decalcifying or the one or more sheets of the bone after the cutting.

21. The process of claim 20, wherein the plurality of perforations are created by punching, burring, drilling, or lasering the sheet.

22. The process of claim 20, wherein the plurality of perforations include channels radiating therefrom.

23. The process of claim 20, where the plurality of perforations comprises one or more perforations having a cross-sectional area that defines a stellate, quadrangular, triangular or hexagonal shape.

24. The method of claim 11, wherein the cutting comprises utilizing a sharp blade to cut the bone.

25. A method for the in vivo repair or replacement of a section of an animal skeletal system comprising:
 affixing, to the section of the animal skeletal system, a flexible organic bone plate comprising a continuous sheet of partially or fully decalcified natural bone having a thickness of 1.5 millimeters or less,
 wherein the continuous sheet comprises a plurality of irregular perforations having serrated edges defined therein configured to facilitate ingrowth of cells and vasculature from preexisting sources of cartilage or bone tissue at a faster rate compared to a bone sheet of similar thickness having regular perforations without serrated edges.

26. The method of claim 25, wherein the plurality of irregular perforations comprise one or more irregular perforations having a cross-sectional area defining a stellate, quadrangular, triangular or hexagonal shape.

27. The method of claim 25, wherein the plurality of irregular perforations include channels radiating therefrom.

28. A flexible organic bone plate comprising a continuous sheet of partially or fully decalcified natural bone, wherein the flexible organic plate is obtained by the process of:
 (i) decalcifying, either partially or completely, a bone from a bone donor;
 (ii) cutting the decalcified bone from step (i) into one or more sheets of decalcified bone having a thickness of 1.5 mm or less using a sharp blade; and
 (iii) creating a plurality of irregular perforations having serrated edges on the one or more decalcified bone sheets of step (ii).

29. The flexible organic bone plate of claim 28, wherein the irregular perforations are created by punching, burring or lasering the one or more decalcified bone sheets.

30. The flexible organic bone plate of claim 28, wherein the irregular perforations comprise a cross-sectional area that defines astellate, quadrangular, triangular or hexagonal shape.

31. The flexible organic bone plate of claim 28, wherein the process further comprises harvesting the bone from the bone donor.

32. The flexible organic bone plate of claim 28, wherein the process further comprises creating channels radiating out from the irregular perforations.

33. The flexible organic bone plate of claim 28, wherein the decalcifying comprises contacting the bone with EDTA, citric acid, hydrochloric acid, or combinations thereof.

34. The flexible organic bone plate of claim 33, wherein decalcifying comprises contacting the bone with citric acid.

35. The flexible organic bone plate of claim 33, wherein the decalcifying comprises contacting the bone with EDTA and citric acid.

36. The flexible organic bone plate of claim 33, wherein the decalcifying comprises contacting the bone with EDTA and hydrochloric acid.

\* \* \* \* \*